United States Patent [19]

Cova et al.

[11] Patent Number: 4,820,385
[45] Date of Patent: Apr. 11, 1989

[54] PURIFICATION OF ALKYL GLYOXYLATE IN A CONTINUOUS COLUMN BY AZEOTROPIC DISTILLATION

[75] Inventors: Dario R. Cova, Kirkwood; John M. Thorman, Chesterfield, both of Mo.

[73] Assignee: Monsanto Company, St. Louis, Mo.

[21] Appl. No.: 156,874

[22] Filed: Feb. 18, 1988

[51] Int. Cl.[4] .......................... B01D 3/36; B01D 3/42; C07C 69/66
[52] U.S. Cl. .......................... 203/2; 203/14; 203/67; 203/69; 203/70; 203/82; 203/84; 203/99; 203/DIG. 18; 203/DIG. 19; 560/177; 560/186
[58] Field of Search ............ 203/2, 14, 67, 69, 70, 203/82, 84, 99, DIG. 18, DIG. 19, DIG. 21, DIG. 23, 28, DIG. 6, 68, 81; 560/177, 186, 180

[56] References Cited

U.S. PATENT DOCUMENTS

| | | | |
|---|---|---|---|
| 3,404,175 | 10/1968 | Mercier | 203/94 |
| 3,432,401 | 3/1969 | Tcherkawsky | 203/94 |
| 3,681,434 | 8/1972 | Neely | 203/14 |
| 4,144,226 | 3/1979 | Crutchfield et al. | 560/180 |
| 4,156,093 | 5/1979 | Christidis | 560/186 |
| 4,234,739 | 11/1980 | Photis et al. | 560/51 |
| 4,250,328 | 2/1981 | Fujita et al. | 203/60 |
| 4,340,748 | 7/1982 | Baltes et al. | 560/177 |
| 4,502,923 | 3/1985 | Dyroff et al. | 203/14 |
| 4,661,208 | 4/1987 | Honma et al. | 203/15 |

FOREIGN PATENT DOCUMENTS

| | | |
|---|---|---|
| 130533 | 1/1985 | European Pat. Off. . |
| 2811480 | 9/1978 | Fed. Rep. of Germany ...... 560/186 |
| 3602274 | 7/1987 | Fed. Rep. of Germany ...... 560/186 |
| 176929 | 10/1982 | Japan . |
| 1050941 | 3/1986 | Japan ................................. 560/186 |
| 109221 | 3/1986 | Japan . |

OTHER PUBLICATIONS

"A Simple and Efficient Synthesis of Ethyl and Methyl Glyoxylate", James M. Hook, *Synthetic Communications*, 14(1), 83–87 (1984).

Primary Examiner—David L. Lacey
Assistant Examiner—V. Manoharan
Attorney, Agent, or Firm—R. Loyer; A. Hoffman; A. Cole

[57] ABSTRACT

An improved process for separating high purity alkyl glyoxylate from complex mixtures containing alkyl glyoxylate, alkyl glycolate, water, alcohol and miscellaneous impurities by an azeotropic distillation operation.

30 Claims, 2 Drawing Sheets

PURIFICATION OF ALKYL GLYOXYLATE IN A CONTINUOUS COLUMN BY AZEOTROPIC DISTILLATION

BACKGROUND OF THE INVENTION

This invention relates to the manufacture of glyoxylic acid esters by oxidation of the corresponding esters of glycolic acid and, more particularly, to an improved process for recovery of water-free and alkanol-free glyoxylic acid ester from the oxidation reaction mass.

Polyacetal carboxylates have been demonstrated to be useful as builders in detergent formulations. Crutchfield U.S. Pat. No. 4,144,226 describes the preparation of polyacetal carboxylates by polymerization of an ester of glyoxylic acid, preferably methyl glyoxylate. The glyoxylic acid ester monomer may be prepared by vapor phase oxidation of the corresponding ester of glycolic acid. Side reactions occurring under the oxidation reaction conditions result in the contamination of the reaction product with water and with an alkanol derived from the ester. To minimize the loss of yield to side reactions, the oxidation reaction is carried out with a deficiency of oxygen, so that the reaction mixture also contains a substantial fraction of unreacted glycolate ester.

In order to obtain a satisfactory yield and a high quality polyacetal carboxylate product from the polymerization reaction, it is necessary that the glyoxylate monomer be of high purity and that, in particular, it be purified to be substantially free of water, alkanol, and unreacted glycolate. In accordance with the process described in U.S. Pat. No. 4,502,923, the product of the oxidation reaction is subject to multiple distillation operations, first at low temperature under vacuum for removal of low boilers, i.e., water and methanol, then at higher temperature under vacuum for removal of glycolate ester as an overhead stream, and finally at atmospheric pressure for removal of glyoxylate ester as an overhead stream. As indicated by an inflection in the vapor/liquid equilibrium curve, more glycolate ester can be removed from a mixture containing glyoxylate ester at low absolute pressure than at atmospheric pressure. The converse is true for glyoxylate ester. Bottoms from the glyoxylate atmospheric pressure distillation contain the glycolate that has not been removed as overhead in the glycolate vacuum still, as well as the hemiacetal of the glycolate and glyoxylate, and other high boilers. This stream is recycled to an earlier step in the process, typically the feed to the low boiler still.

Glyoxylate ester reacts with water to form the hydrate, and with both alkanol and glycolate to form the corresponding hemiacetals. These are equilibrium reactions which may proceed in either direction not only in the reaction step but also in the distillation steps and beyond. Although the first vacuum distillation step may be effective for removal of free water and alkanol, glyoxylate hydrate and glyoxylate/alkanol hemiacetal remain in the the still bottoms and are carried forward to subsequent steps where they may be decomposed to form additional free water and alkanol. Under the conditions of the atmospheric glyoxylate still, in particular, removal of glyoxylate ester from the liquid phase tends to promote the decomposition of hydrate and alkanol hemiacetal.

Various efforts have been made in the art to produce a glyoxylate monomer substantially free of water and alkanol. In one such process, described in Chou et al. U.S. Pat. No. 4,502,923, methyl glycolate is added in the vacuum distillation of low boilers, thereby converting free methyl glyoxylate to the glycolate/glyoxylate hemiacetal in accordance with that equilibrium reaction. By thus reducing the concentration of free glyoxylate, the addition of glycolate promotes decomposition of the glyoxylate hydrate and methanol hemiacetal in the vacuum distillation, so that the water and methanol they contain can be substantially removed in that step. However, the effectiveness of this procedure is limited by the equilibrium relationships, and quantitative removal of water and alkanol can be achieved only at the expense of dealing with a large fraction of glycolate/glyoxylate hemiacetal in the bottoms product. A high concentration of glycolate in the system reduces the productivity of the process and increases the energy requirements of the separation steps.

Christidis U.S. Pat. No. 4,156,093 describes a process in which hemiacetal esters of glyoxylic acid are produced by reacting aqueous glyoxylic acid with an excess of alkanol, preferably butanol, and simultaneously dehydrating the reaction product by an azeotropic distillation in which the alkanol serves as the azeotroping agent, alkanol being refluxed to the reaction pot. Thereafter, the excess alkanol is distilled off under vacuum, the residue treated with phosphoric acid to convert the hemiacetal ester to the aldo-ester, and the residue redistilled under vacuum to recover the aldo-ester.

Japanese patent No. 57-176,929 describes a process in which glyoxylic acid ester is produced by pyrolizing a hemiacetal in a distillation column in the presence of benzene, the alkanol produced on pyrolysis being removed in the form of a benzene/alcohol azeotrope.

German Offenlegungsschrift No. 33 23 372 describes a process in which a glyoxylic acid ester is produced by oxy-dehydrogenation, apparently of a glycolic acid ester. An entrainer, typically pentane or cyclohexane, is added to the reaction mixture, after which the resulting mixture is fed to the central point of a fractionating column. Water of reaction, other low boilers and entrainer distill off the top of the column, and glyoxylic acid ester is left as a sump product.

Japanese patent No. 171789 describes a process for obtaining glyoxylic acid ester obtained by reacting 1-4 carbon alcohols, in the presence of azeotropic solvents, benzene and dichloroethane. The reaction mixture is distilled to recover the ester.

SUMMARY OF THE INVENTION

Among the several advantages of the present invention may be noted the provision of an improved process for the manufacture of lower alkanol esters of glyoxylic acid by oxidation of glycolic acid esters; the provision of such a process which provides a high purity product; the provision of such a process which can be operated at high productivity; the provision of such a process which can be operated to produce glyoxylate ester in high yields; the provision of such a process which does not generate excessive recycle streams; the provision of such a process which produces a product which can be polymerized to provide a high quality polymeric acetal carboxylate; the provision of such a process which produces a product which can be polymerized to produce a high quality detergent builder composition; and the provision of a process for producing a high quality polyacetal carboxylate.

Briefly therefore, the present invention is directed to an improvement in a process for the preparation of an alkyl ester of glyoxylic acid, the process comprising oxidizing an ester of glycolic acid to the glyoxylic acid ester and producing a monomer mixture comprising the glyoxylic acid ester, the glycolic acid ester, alcohol and water. The crude monomer mixture is then treated to remove the majority of low boilers. The improvement comprises recovering glyoxylic acid ester from the treated monomer mixture by an azeotropic distillation operation. In the distillation operation, the monomer mixture is fed to a multi-stage monomer distillation column, in the upper stages of which a concentration of an azeotroping agent is maintained, the azeotroping agent forming a low boiling binary azeotrope with water and being immiscible with water to permit gravity separation of water from the agent. Vapor from the uppermost stage of the monomer column is condensed, thereby producing an overheads condensate. The azeotroping agent is separted from the water of the overheads condensate and returned above the uppermost stage of the monomer column as reflux. The glyoxylic ester fraction is removed from the side of the column at a stage intermediate the feed point and the uppermost stage; and a fraction comprising glycolic acid ester, glyoxylic acid ester hydrate and glyoxylic acid ester hemiacetals is removed from the bottom of the column.

The invention is also directed to an improvement in a procress of the aforesaid type in which a reaction product containing glyoxylic acid ester is produced by oxidizing an ester of glycolic acid, and the reaction mixture is distilled to remove low boilers and produce a monomer mixture containing residual water. The improvement comprises an azeotropic distillation operation of the type described above.

The invention is further directed to an improved process for the preparation of an alkyl ester of glyoxylic acid, the process comprising oxidizing an ester of glycolic acid to said glyoxylic acid ester and producing a monomer mixture comprising the glyoxylic acid ester. The improvement comprises recovering the glyoxylic acid ester from the monomer mixture by a distillation operation. In the distillation operation, the monomer mixture is first treated to remove the majority of low boilers and is then distilled in a monomer column to produce a bottoms fraction comprising glycolic acid ester, glyoxylic acid ester hydrate, and glyoxylic acid hemiacetals, and a glyoxylic ester fraction comprising the glyoxylic acid ester and water. The glyoxylic acid ester fraction is fed to a multi-stage finishing distillation column. A concentration of azeotroping agent is maintained in the upper stages of the finishing column, the azeotroping agent forming a low boiling binary azeotrope with water and being immiscible with water to permit a gravity separation of water from said agent. Vapor from the uppermost stage of the finishing column is condensed, thereby producing a finishing column overheads condensate. The azeotroping agent is separated from the water of the finishing column overheads condensate and the azeotroping agent returned to the uppermost stage of the finishing column as reflux. Dehydrated glyoxylic ester fraction is removed from the side of the finishing column at a stage intermediate the finishing column feed point and the finishing column uppermost stage.

The invention is also directed to improvement in a process for the preparation of an alkyl ester of glyoxylic acid, the process comprising oxidizing an ester of glycolic acid to said glyoxylic acid ester and producing a monomer mixture comprising the glyoxylic acid ester, and separating a glyoxylic ester fraction from the monomer mixture. The improvement comprises removing residual moisture from the glyoxilic acid ester fraction by an azeotropic distillation operation comprising the finishing column distillation operation described above.

Other objects and features will be in part apparent and in part pointed out hereinafter.

DESCRIPTION OF THE PREFERRED EMBODIMENTS

Figure 1:
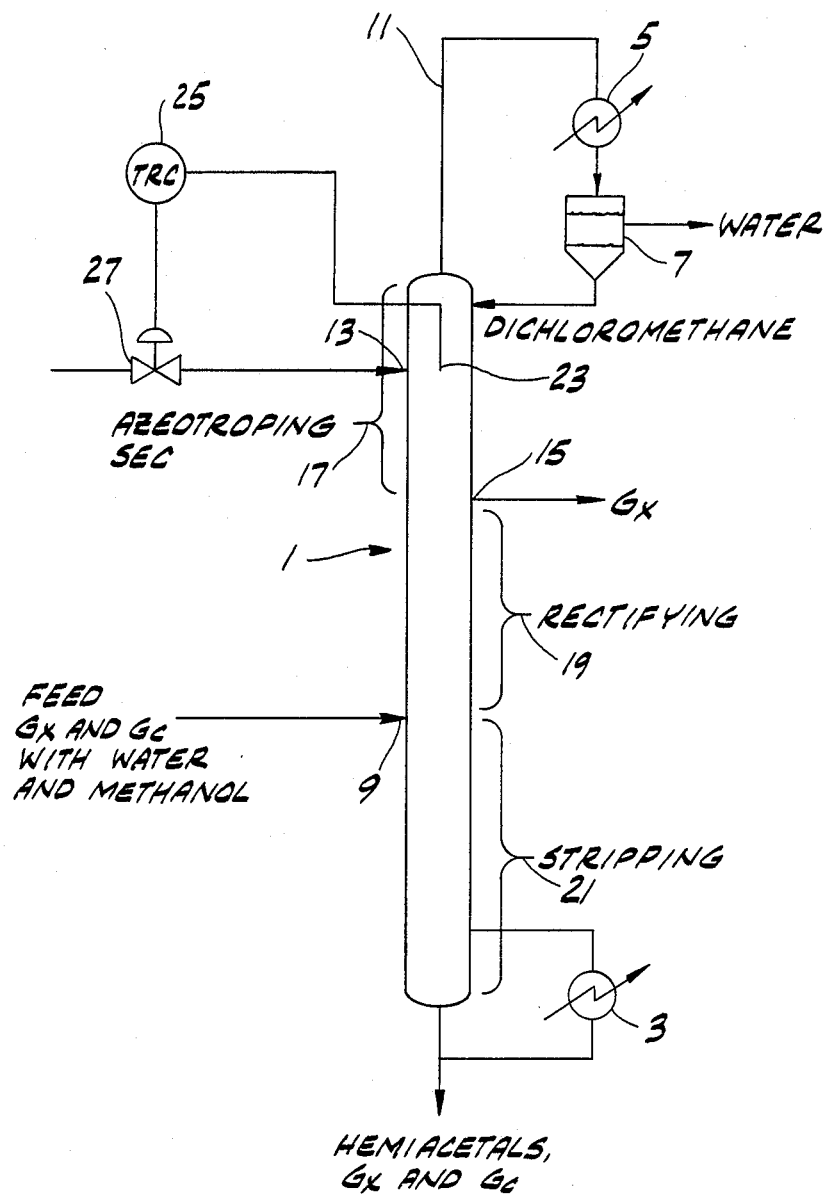
FIG. 1 is schematic flow diagram illustrating the monomer distillation process of the invention.

In accordance with the present invention, it has been discovered that an azeotropic distillation operation can be used to efficiently separate residual moisture and alkanols from the treated reaction mass obtained in the oxidation of a glycolic acid ester to a glyoxylic acid ester. More particularly, it has been found that, by incorporation of an azeotroping agent which forms a low boiling binary azeotrope with water, the residual water can be essentially quantitatively removed as as part of an overheads condensate, and the desired glyoxylic acid ester fraction removed as a column side draw above the feed point but below the point at which the azeotropic agent is concentrated in the column. Moreover, it has been found that the monomer separation may be carried out conveniently and advantageously at atmospheric pressure.

Removal of residual water is substantially accomplished in the same atmospheric distillation operation in which the principal separation of glycolic acid ester from glyoxylic acid ester monomer is carried out. However, to achieve maximum dryness of the glyoxylic acid ester, the side draw fraction is preferably fed to another column, the finishing column, in which a similar azeotropic distillation is carried out, again preferably at atmospheric head pressure, for additional removal of residual moisture. The finishing column also effects separation of residual alkanol from the glyoxylic acid ester fraction, the alkanol showing up in the bottoms of the finishing column.

The bottom fractions from both the monomer distillation and finishing distillation may be recycled to the oxidation reaction stage along with unreacted glycolic acid. This allows full recovery of the raw material value of these by-products. Because the reactions which form hydrate and hemiacetals in the oxidation step are reversible, there is no accumulation of hydrate or hemiacetals in the system, but instead almost all are ultimately converted to the desired glyoxylic acid ester product. Only the formation of high boilers, degradation from modest side reactions, and very minor losses to the atmosphere detract from essentially quantitative yield of the desired product.

Moreover, the process of the invention provides for the preparation of a high quality glyoxylic acid ester product in high yield without the necessity of operating with substantial excesses of glycolic acid ester in the system. Thus, both the productivity penalty and yield loss associated with the presence of excess glycolic acid ester are avoided. The process of the invention further provides high quality and yield without the necessity of chemical reagents such as phosphoric acid from conversion of the hemiacetal to the desired ester. The only foreign material in the system is the azeotropic agent, and this agent is highly volatile and readily separated from the glyoxylic acid ester.

The process of the invention is especially advantageous in the preparation, isolation and purification of methyl glyoxylate. However, it is effective for the production of other lower alkyl glyoxylates in high yield and quality. In particular, the process may be used in the production of ethyl glyoxylate, n-propyl glyoxylate, isopropyl glyoxylate, and various butyl glyoxylates.

A number of azeotroping agents may be used in carrying out the process of the invention. There are, however, certain criteria which govern the selection of the azeotroping agent. Thus, the agent should not be reactive with any of the components of the system, especially glyoxylic acid or the glyoxylic acid ester. It should not only be sufficiently immiscible with water to effect rapid and clean separation of the phases of the overheads condensate, but it should have limited solubility in water to minimize overheads losses and any environmental problems that might arise from its contamination of the overheads condensate water fraction, which is discarded. It should, of course, form a low boiling binary azeotrope with water, and also have an atmospheric boiling point sufficiently below that of the glyoxylic acid ester to provide for separation of water and ester.

Generally suitable azeotroping agents include aromatic hydrocarbons and halogenated alkanes. Particularly preferred is methylene chloride, but 1,1,1-trichloroethane and benzene are also advantageously used.

Illustrated schematically in FIG. 1 is a continuous column system adapted for carrying out the process of the invention. Shown at 1 is a multi-stage distillation column having a reboiler 3, a condenser 5 and a condensate receiver and separator 7. A mixture containing a glyoxylic acid ester and glycolic acid ester is fed continuously to the column at feed point 9. Overheads condensate leaves the top of the column through overheads vapor line 11 and is condensed in condenser 5, the condensate flowing by gravity into receiver 7 where it separates into an aqueous fraction and an organic fraction comprising the azeotropic agent. The water is discarded and the azeotroping agent is returned to the column at the top stage as reflux. Makeup azeotroping agent is fed to the column at point 13.

A glyoxylic ester fraction having a high glyoxylic ester content and relatively low water content is withdrawn at side draw 15 which is located several stages below the point at which makeup azeotroing agent is introduced. Preferably the glyoxylic ester fraction is in the liquid state. From an operational standpoint, the column is divided into an azeotroping section 17 above the side draw 15, a rectifying section 19 between the feed point and the side draw, and a stripping section 21 below the feed point. Methanol, glycolate ester and hemiacetals are drawn off from the bottom of the column along with glyoxylate ester.

Control of the upper stages of the column is also illustrated in FIG. 1. This control system comprises a temperature probe 23 located in a control stage at or near point 13, a temperature recorder/controller 25 which receives a signal from probe 23, and a control valve 27 which admits makeup azeotroping agent to the column in response to a signal from controller 25. The system is set to maintain a temperature at the control stage a few degrees higher than the boiling temperature of the binary azeotrope at the pressure maintained at the top of the column. As the temperature rises due to vent losses or water solubility and entrainment losses of azeotroping agent, controller 25 causes valve 27 to admit additional azeotroping agent. As the temperature falls back to the set point, valve 27 is throttled down or closed.

Figure 2:
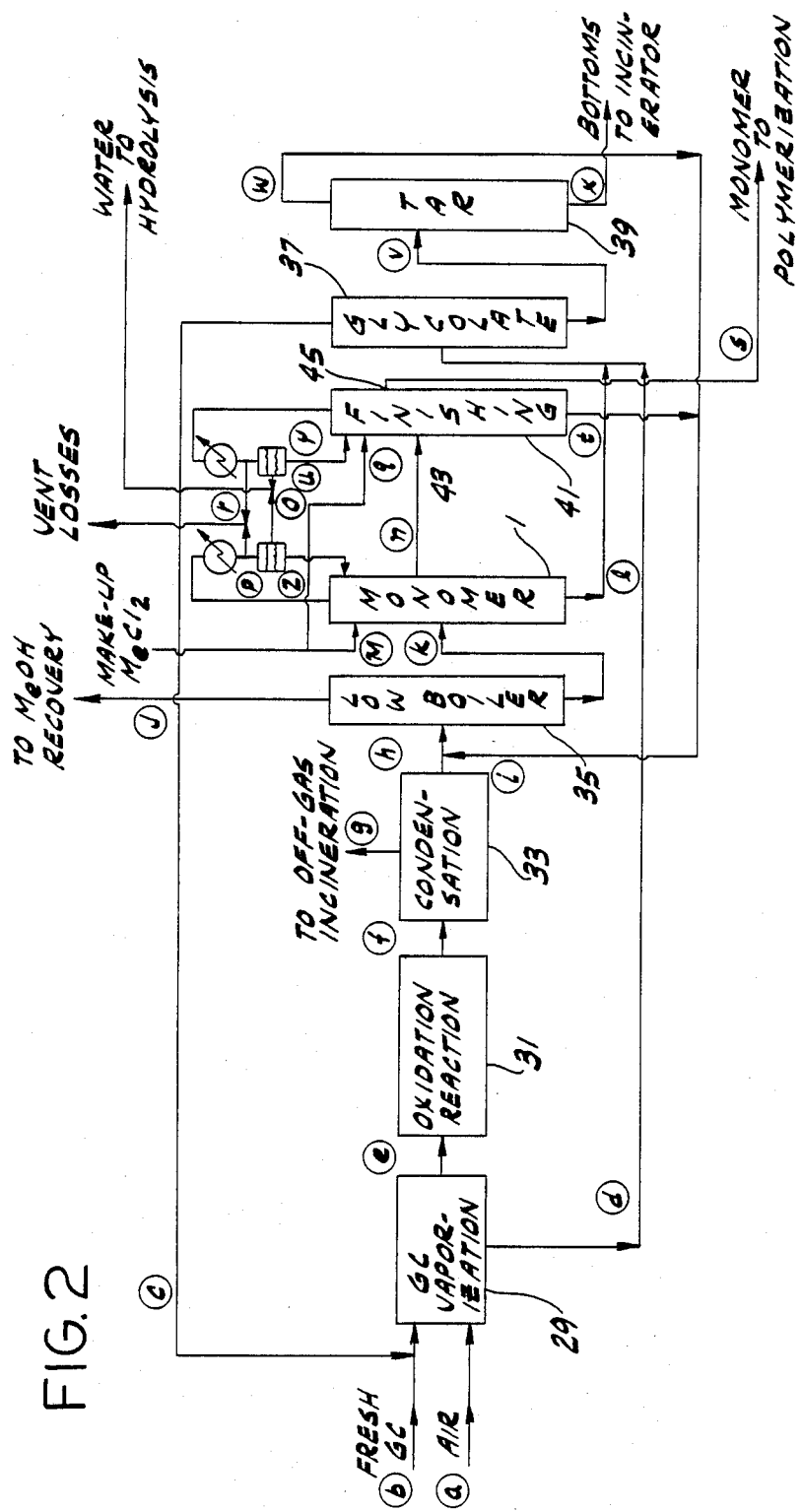
FIG. 2 is a schematic diagram illustrating the combined monomer and finishing distillation operation of the invention.

As noted above, the novel separation process of the invention may be implemented in a column for the separation of glyoxylic acid ester monomer from glycolic acid ester. However, as illustrated in FIG. 2, the monomer column is preferably followed by a finishing column in which additional residual moisture and alkanol are removed from the glyoxylic ester fraction obtained from the monomer column. In a further but generally less preferred alternative, the monomer column can be operated without an azeotroping agent, thus producing a glyoxylic acid ester overhead fraction which is dehydrated in a finishing column operated in accordance with the improved process of the invention. However, because this alternative puts an extra load on the finishing column without significant savings in the operation of the monomer column, the arrangement of FIG. 2 is normally preferred.

FIG. 2 shows a system in which glycolic acid ester and air are fed continuously to a glycolic ester vaporizer 29 which generates a vapor phase reactant mixture that is, in turn, fed to an oxidation reactor 31. The oxidation reaction produces a gaseous mixture of alkyl glyoxylate, alkyl glycolate, water, alkanol, carbon monoxide, carbon dioxide, residual oxygen, and nitrogen. This gaseous mixture is treated by passing it into a condenser 33 from which the noncondensibles are vented, and where a condensed phase mixture is produced comprising alkyl glyoxylate, alkyl glycolate, water, and alkanol. This mixture is fed to a low boiler still 35 where a major portion of the water and a substantial portion of alkanol are taken off under vacuum.

Any suitable treatment may be provided to condense the desired products and to remove the majority of the undesired low boilers. Typically, such treatment is performed as described above and shown in FIG. 2. However, alternative means to perform these functions may be employed. For example, the oxidation reaction product may be passed through an absorber to remove low boilers and recover the desired product. Alternatively, a partial condenser may be employed wherein a major amount of the low boilers remain gaseous while the desired product is condensed and collected.

The bottom fraction from the low boiler still constitutes the feed mixture for the monomer still 1 which is arranged and operated as illustrated in FIG. 1 and discussed above. The bottom fraction from the monomer still is fed to a glycolate column 37 operated under vacuum, the overheads of which are recycled to the vaporizer 29, and the bottom fraction of which is fed to a vacuum still 39 for recovery of residual glycolate and glyoxylate that is recycled to the low boiler column 35. The feed for still 37 also includes unvaporized material from vaporizer 29. Tars and other high boilers from the bottom of still 39 are discarded.

The side draw from the monomer still is fed continuously to the multi-stage finishing still 41 via feed point 43. Still 41 is arranged and operated in the manner broadly described above with reference to FIG. 1. The side draw from point 45 on still 41 constitutes a dehydrated glyoxylic ester fraction suitable for use in the polymerization reaction for the preparation of a polyacetal carboxylate. Bottoms from finishing column 41 are mixed with overheads from still 39 and recycled to the low boiler still 35.

Typically, the feed mixture to the monomer still contains 40–50% by weight alkyl glyoxylate, 45–55% by weight alkyl glycolate, 1 to 2.5% by weight alkanol, and 0.3–1% water. Referring again to FIG. 1, the monomer stil typically has 70 to 90 sieve trays and is preferably operated at atmospheric pressure, with feed point 9 being at between about the 40th and 60th tray. Operation at atmospheric pressure represents an optimal comprise between separation efficiency and degradation of product, since higher temperatures give a higher equilibrium fraction of glyoxylate ester in the vapor phase but also conduce to thermal degradation of product. Where the top of the column is maintained at atmospheric pressure, the temperature at the bottom of the column is typically 150°–170° C. An azeotroping agent is concentrated in the top five to ten sieve trays of the column, with the temperature control point and azeotroping agent makeup addition point being at about the fifth to tenth sieve tray. Vapor leaving the top sieve tray is essentially comprised of the binary azeotrope. Upon condensation, the moisture component of the azeotrope is drawn off and discarded while the azeotroping agent is returned to the top tray of the column as reflux. Side draw 15 for the glyoxylic acid ester fraction is at between about tray five and about tray fifteen, but is in any case at least about five trays below point 13 for addition of makeup azeotroping agent. Between about 10% and about 50%, preferably about one third, of the liquid phase flowing to the side draw tray is continuously drawn off the column at that point as the glyoxylic acid ester fraction. For a feed mixture having the composition referred to above, the glyoxylic ester fraction may contain 85–95% by weight alkyl glyoxylate, 2–4% by weight alkyl glycolate, 3–7% by weight alkanol, and 0.3–1% water.

Stages inside of column 1 can be established in any conventional manner as, for example, by bubble cap trays or sieve trays. However, in order to minimize decomposition of alkyl glyoxylate or alkyl glycolate during column operations, the residence time in the column is preferably kept to a minimum. Accordingly, sieve trays are preferred to bubble cap trays. The use of a packed column is particularly preferred because this provides the least liquid holdup and the shortest residence time. If packing is employed, the residence time inside the column can be limited to between about 4 and about 7 minutes, between about 0.8 and about 2 minutes in the stripping section. The use of packing also allows column pressure drop to be limited to between about 30 and about 70 mm. Hg.

To minimize degradation of product, it is also important that oxygen be substantially excluded from the column during monomer still operation. Preferably, the column is purged with an inert gas, such as nitrogen, prior to column startup, and an inert gas blanket is maintained in the column during its operation.

Finishing column 41 typically contains between about thirty and about fifty equilibrium sieve trays, with feed point 43 at between about the 20th and 40th sieve tray. Like the monomer column, the finishing column is preferably operated at atmospheric pressure so that alkyl glycolate remaining in the feed stream is quantitatively separated from the glyoxylate fraction. Thus, temperature at the bottom of the column is in the range of 125°–150° C. The system at the upper portion of the column, i.e., above the feed sieve tray, is substantially identical to that for the monomer column. Thus, the azeotroping agent is concentrated in the top five to ten sieve trays of the column, with the temperature control point and azeotroping agent makeup addition point being at about the fifth to tenth sieve tray. Vapor having a composition approximating the binary azeotrope is condensed and separated, with the azeotroping agent being refluxed to the top sieve tray of the column. Side draw 45 of the dehydrated glyoxylic acid ester fraction is at between about sieve tray five and about sieve tray fifteen, and in any case at least about five sieve trays below the point at which makeup azeotroping agent is added. Between about 10% and about 50%, preferably about one-fourth of the liquid flowing to the side draw stage is removed as the side draw fraction. The control system is as described in FIG. 1. Oxygen is excluded from the column, preferably by means of inert gas as described above with respect to the monomer column. Here also, sieve trays are preferred to bubble cap trays, and a packed column is most preferred. By use of packing the residence time in the finishing column can be limited to about 5 minutes, no more than about 1 minute in the stripping section, and pressure drop through the column is limited to between about 20 and about 40 mm. Hg.

For a feed stream from the monomer column containing 85–95% by weight alkyl glyoxylate, 2–4% by weight alkyl glycolate, 3–7% by weight alkanol, and 0.3–1% water, the finishing column is operated continuously to produce a dehydrated glyoxylic ester fraction containing 97–99% by weight glyoxylic acid ester, less than 0.2% by weight of combined water and alkanol, the balance being essentially constituted of the azeotroping agent. The bottom fraction from the finishing column comprises typically 75–85% by weight alkyl glyoxylate, 3–10% alkyl glycolate, 7–15% by weight alkanol, and less than 0.8% water.

The following examples illustrate the invention.

EXAMPLE 1

Using a laboratory equipment arrangement of the type illustrated in FIGS. 1 and 2, a low boiler column, a monomer column, a finishing column, a glycolate column and a tar column were set up and operated continuously in the manner described above for recovery of dehydrated methyl glyoxylate from a low boiler column feed mixture containing methyl glyoxylate, methyl glycolate, methanol, water, and minor amounts of glyoxylic acid, glycolic, acetic acid, formic acid, and methylmethoxyacetate. The feed also contained a minor fraction of methylene dichloride azeotroping agent which had been recycled from the glycolate column overheads and finishing column bottoms. Each of the low boiler, monomer, and finishing columns contained sieve trays, while the glycolate column was provided with 55 mm OD Koch Sulzer packing. The low boiler column contained thirty trays, with the feed at the fifteenth tray. The monomer column contained eighty trays, with the feed at the fiftieth tray and the side draw at the tenth tray. The finishing column contained forty trays, with the feed at the thirtieth tray and the side draw at the tenth tray. There were fifteen equilibrium stages in the glycolate column, nine in the rectifying section above the feed and six in the stripping section below the feed. The tar column contained five sieve trays, all in the rectifying section. Conditions under which the several columns were operated are set forth in Table 1.

EXAMPLE 2

A plant is operated in accordance with the flow sheet of FIG. 2 to produce methyl glyoxylate monomer from methyl glycolate. A material balance is made on the plant operations. The results of this material balance, together with the conditions of the various steps of the process, are set forth forth in Table 3. The designations of process streams correspond to the letter labels set forth in FIG. 2.

TABLE 1
COLUMN OPERATING CONDITIONS

| Column | # Actual Strip. | Trays Rectif. | Azeo. | Head Press. mm Hg | Reflux Ratio | Reboiler | Feed Tray | Temp. Preheater | Reflux Cntrl. Tray | Side-draw Tray | Azeotrope Cntrl. Tray | Top Temp. | P** mm Hg |
|---|---|---|---|---|---|---|---|---|---|---|---|---|---|
| Lowboiler | 15 | 15 | 0 | 50 | 1.5:1 | 95 | 78 | 68 | 45 | — | — | 33–35 | 20 |
| Monomer** | 30 | 40 | 10 | Atm. | 2:1$^a$ | 157 | 148 | 132 | 137 | 127 | 43 | 40 | 70 |
| Finishing** | 10 | .20 | 10 | Atm. | 3:1$^a$ | 134 | 121 | 115 | 120 | 118 | 43 | 40 | 35 |
| Glycolate | 6* | 9* | 0 | 35 | 1:1 | 88 | 70 | 66 | 68 | — | — | 66 | 3 |
| Tar | 0 | 5 | 0 | 50 | 0:1 | 150 | 100 | 100 | — | — | — | 68 | 3 |

*FT of Koch Sulzer Packing, 55 mm OD.
**Atmospheric Head Pressure - Temperature Profile
***Bench Unit P
$^a$in monomer and finishing columns, reflux ratio refers to ratio of liquid routed to stage below side draw vs. liquid removed from column as side draw.

A material balance was made on the operation of the columns of this example. The results of this material balance are set forth in Table 2. Labels of streams are as shown in FIG. 2.

TABLE 2
TYPICAL MONOMER SEPARATIONS STREAM COMPOSITIONS WT % (PPM)

| | Low Boiler Feed | Low Boiler Distillate | Monomer Feed | Monomer Btms. | MeCl$_2$ Makeup | Monomer Sdw. | H$_2$O to Hydrolysis | Monomer Col. Vent |
|---|---|---|---|---|---|---|---|---|
| Component | i | j | k | l | m | n | o | p |
| Water | 3.70 | 73.81 | .50 | .06 | | 0.60 | 77.37 | |
| Methanol | 2.71 | 23.52 | 1.76 | .06 | | 4.98 | 7.04 | |
| Methyl Glyoxylate | 43.87 | | 45.71 | 21.80 | | 91.03 | | |
| Methyl Glycolate | 49.34 | | 51.42 | 77.19 | | 2.70 | | |
| Methylene Chloride | | | | | 100 | 0.20 | 1.13 | 100 |
| MMA | 0.16 | 1.81 | | | | | | |
| Dimethyl Tartronate | | | | | | | | |
| Formaldehyde | 0.2 | 0.81 | (600) | (40) | | .16 | 13.5 | |
| Formic Acid | (110) | (15) | (90) | (37) | | (280) | | |
| Glyoxylic Acid | .15 | (30) | .15 | .18 | | (510) | | |
| Glycolic Acid | (200) | (15) | (280) | (765) | | (15) | | |
| Acetic Acid | (350) | (30) | (290) | | | .26 | | |
| Others | | | | 0.63 | | | 0.96 | |

| | Makeup MeCl$_2$ | Finish Col. Vent | Monomer | Finish Btm. | Water to Hydrolysis | Gly. Bottom | Tar Dist. | Tar Btms. | Glycolate Dist. |
|---|---|---|---|---|---|---|---|---|---|
| Component | q | r | s | t | u | v | w | x | c |
| Water | | | 0.10 | 0.60 | 67.0 | .05 | .24 | 0.1 | .06 |
| Methanol | | | 0 | 10.96 | 6.7 | .05 | .06 | 0.1 | .06 |
| Methyl Glyoxylate | | | 98.27 | 81.51 | | 37.22 | 37.03 | 3.0 | 1.00 |
| Methyl Glycolate | | | | 5.96 | | 60.90 | 62.57 | 9.0 | 98.90 |
| Methylene Chloride | 100 | 100 | 1.50 | | 1.0 | | | | (50–100) |
| MMA | | | | | | | | | |
| Dimethyl Tartronate | | | | | | | | | |
| Formaldehyde | | | (460) | (250) | 24.6 | (10) | (17) | (50) | (30) |
| Formic Acid | | | (370) | (100) | | (55) | (60) | (105) | (30) |
| Glyoxylic Acid | | | (280) | 0.40 | | .25 | (770) | .4 | (40) |
| Glycolic Acid | | | | | | (455) | (225) | .12 | (20) |
| Acetic Acid | | | (150) | 0.25 | | | | | |
| Others | | | | .29 | 0.70 | 1.34 | | 87.3 | |

TABLE 3

| | a | b | c | d | e | f | g | h | i | j | k | l |
|---|---|---|---|---|---|---|---|---|---|---|---|---|
| Water | 2.60 | 1.12 | .08 | | 3.80 | 19.40 | 5.20 | 16.20 | 16.70 | 14.50 | 2.20 | .16 |
| Methanol | | .02 | .08 | | .10 | 4.90 | .20 | 4.70 | 12.20 | 4.60 | 7.60 | .16 |
| Methyl Glyoxylate | | | 1.20 | .20 | 1.00 | 87.30 | .10 | 87.20 | 198.30 | | 198.30 | 61.90 |
| Methyl Glycolate | | 111.56 | 124.20 | 4.40 | 231.06 | 125.40 | .40 | 125.00 | 223.10 | | 223.10 | 219.00 |

TABLE 3-continued

| | | | | | | | | | | | |
|---|---|---|---|---|---|---|---|---|---|---|---|
| Nitrogen | 67.80 | | | | 67.80 | 67.80 | 67.80 | | | | |
| Oxygen | 20.70 | | | | 20.70 | 1.60 | 1.60 | | | | |
| Carbon Monoxide | | | | | | 5.10 | 5.10 | | | | |
| Carbon Dioxide | | | | | | 8.40 | 8.40 | | | | |
| Hydrogen | | | | | | .40 | 0.40 | | | | |
| Acids | | .06 | | .005 | .08 | .16 | | .16 | .32 | | .32 | .16 |
| Others | | .10 | | .10 | .30 | 2.40 | | 2.40 | 2.40 | | 2.40 | 2.40 |
| Methylene Chloride | | | | | | | | | | | | |
| Total | 91.10 | 112.86 | 125.60 | 4.70 | 324.86 | 324.86 | 89.20 | 235.66 | 453.62 | 19.10 | 434.52 | 283.74 |
| Temperature C. | 130 | 30 | 66 | 170 | 170 | 560 | 10–15 | 10–15 | 67 | 33 | 114 | 165 |
| Pres. (PSIG) TORR | (20) | ATM | ATM | ATM | (15) | (10) | (10) | (10) | | 50 | 155 | 953 |
| Density | | | | | | | | | | | | |
| Viscosity | | | | | | | | | | | | |

| | m | n | o | p | q | r | s | t | u | v | w | x |
|---|---|---|---|---|---|---|---|---|---|---|---|---|
| Water | | .90 | 1.10 | | | | .08 | .40 | .40 | .08 | .08 | |
| Methanol | | 7.50 | .10 | | | | | 7.50 | .04 | .08 | .08 | |
| Methyl Glyoxylate | | 136.40 | | | | | 81.00 | 55.40 | | 60.90 | 55.70 | 5.30 |
| Methyl Glycolate | | 4.10 | | | | | | 4.10 | | 103.40 | 94.00 | 5.30 |
| Nitrogen | | | | | | | | | | | | |
| Oxygen | | | | | | | | | | | | |
| Carbon Monoxide | | | | | | | | | | | | |
| Carbon Dioxide | | | | | | | | | | | | |
| Hydrogen | | | | | | | | | | | | |
| Acids | | .16 | | | | | .08 | .16 | | .16 | | .16 |
| Others | | | .009 | | | | | | .003 | 2.40 | | 2.40 |
| Methylene Chloride | .4 | .32 | .016 | .08 | 1.00 | .08 | 1.22 | | .006 | | | |
| Total | .4 | 149.30 | 1.23 | .08 | 1.00 | .08 | 82.38 | 67.40 | .45 | 163.10 | 149.50 | 13.04 |
| Temperature C. | 25 | 128 | 35 | 15 | 25 | 15 | 118 | 145 | 35 | 86 | 68 | 155 |
| Pres. (PSIG) mmHg | | | | | | | | 925 | | 38 | 50 | 60 |
| Density | | | | | | | | | | | | |
| Viscosity | | | | | | | | | | | | |

In view of the above, it will be seen that the several objects of the invention are achieved and other advantageous results attained.

As various changes could be made in the above methods without departing from the scope of the invention, it is intended that all matter contained it the above description or shown in the accompanying drawings shall be interpreted as illustrated and not in a limiting sense.

What is claimed is:

1. In a process for the preparation of an alkyl ester of glyoxylic acid, said process comprising oxidizing an alkyl ester of glycolic acid to said glyoxylic acid ester and producing a monomer mixture comprising a glyoxylic acid ester, a glycolic acid ester, alcohol and water, the improvement which comprises treating said monomer mixture to remove low boilers and recovering said glyoxylic acid ester from said treated monomer mixture by an azeotropic distillation operation, said operation comprising:

feeding said treated monomer mixture to a multistage monomer distillation column;

maintaining a concentration of an azeotroping agent in the upper stages of said monomer column, said azeotroping agent forming a low boiling binary azeotrope with water and being immiscible with water to permit a gravity separation of water from said agent;

condensing vapor from the uppermost stage of said monomer column, thereby producing an overheads condensate;

separating the azeotroping agent from the water of said overheads condensate and returning the azeotroping agent to the uppermost stage of said monomer column as reflux;

removing a glyoxylic ester fraction from said column at a stage intermediate the feed point and said uppermost stage; and removing from the bottom of said monomer column a fraction comprising glycolic acid ester, a glyoxylic acid ester hydrate, and a glyoxylic acid ester hemiacetals.

2. A process as set forth in claim 1 wherein said azeotroping agent is not reactive with glyoxylic acid or said glyoxylic acid ester, has a low solubility in water, has a density different from water to provide separation therefrom, and forms a low boiling azeotrope with water, said azeotrope having an atmospheric boiling point below that of said glyoxylic acid ester to provide for separation of water from said ester.

3. A process as set forth in claim 2 wherein said azeotroping agent is selected from the group consisting of methylene dichloride, 1,1,1,-trichloroethane, and benzene.

4. A process as set forth in claim 3 wherein said azeotroping agent comprises methylene dichloride.

5. A process as set forth in claim 1 wherein said azeotropic distillation operation is carried out at a substantially atmospheric head pressure.

6. A process as set forth in claim 5 wherein the temperature within said monomer column is measured at a control stage therein, said control stage being above the stage at which the glyoxylic acid ester fraction is withdrawn from the side of the column but below said uppermost stage, and said temperature is controlled by controlling addition of said azeotroping agent to said monomer column above said stage at which said glyoxylic acid ester fraction is withdrawn.

7. A process as set forth in claim 6 wherein said monomer column contains between about 70 and about 90 sieve trays and said monomer mixture is fed to said monomer column at between about the fortieth sieve tray and about the sixtieth sieve tray.

8. A process as set forth in claim 7 wherein said glyoxylic acid fraction is withdrawn from said monomer column at between about the fifth and about the fifteenth sieve tray.

9. A process as set forth in claim 8 wherein said glyoxylic acid fraction constitutes about one third of the liquid flowing to the stage at which said fraction is withdrawn.

10. A process as set forth in claim 9 wherein the temperature at the bottom of said monomer column is controlled at between about 150° and about 170° C.

11. A process as set forth in claim 1 wherein the temperature at the bottom of said monomer column is controlled at between about 150° and about 170° C.

12. A process as set forth in claim 1 wherein oxygen is substantially excluded from said monomer column during said azeotropic distillation operation.

13. A process as set forth in claim 12 wherein an inert gas purge is passed through said monomer column prior to said operation.

14. A process as set forth in claim 12 wherein a blanket of inert gas is maintained in the head of said monomer column during said operation.

15. A process as set forth in claim 1 further comprising removing a residual water from said glyoxylic acid ester fraction by a finishing azeotropic distillation operation, said finishing distillation operation comprising:
feeding said glyoxylic acid ester fraction to a multistage finishing distillation column;
maintaining a concentration of an azeotroping agent in the upper stages of said finishing column, said azeotroping agent forming a low boiling binary azeotrope with water and being immiscible with water to permit a gravity separation of water from said agent;
condensing vapor from the uppermost stage of said finishing column, thereby producing an finishing column overheads condensate;
separating the azeotroping agent from the water of said finishing column overheads condensate and returning the azeotroping agent to the uppermost stage of said finishing column as reflux;
removing a substantially dehydrated glyoxylic ester fraction from the side of said finishing column at a stage intermediate the feed point and said uppermost stage; and
removing from the bottom of said finishing column a fraction containing hemiacetals of glyoxylic acid ester with alkanol and alkyl glycolate.

16. In a process for the preparation of an alkyl ester of glyoxylic acid, said process comprising oxidizing an ester of glycolic acid to a glyoxylic acid ester and producing a monomer mixture comprising said glyoxylic acid ester, the improvement which comprises treating said monomer mixture to remove low boilers and separating a glyoxylic acid ester fraction from said treated monomer mixture, removing a residual moisture from said glyoxylic acid ester fraction by an azeotropic distillation operation, said operation comprising:
feeding said glyoxylic acid ester fraction to a multistage finishing distillation column;
maintaining a concentration of an azeotroping agent in the upper stages of said finishing column, said azeotroping agent forming a low boiling binary azeotrope with water and being immiscible with water to permit a gravity separation of water from said agent;
condensing vapor from the uppermost stage of said finishing column, thereby producing a finishing column overheads condensate;
separating the azeotroping agent from the water of said finishing column overheads condensate and returning the azeotroping agent to the uppermost stage of said finishing column as reflux;
removing a substantially dehydrated glyoxylic ester fraction from the side of said column at a stage intermediate the feed point and said uppermost stage; and
removing from the bottom of said finishing column a fraction containing hemiacetals of glyoxylic acid ester with alkanol and alkyl glycolate.

17. A process as set forth in claim 16 wherein said azeotroping agent is not reactive with glyoxylic acid or said glyoxylic acid ester, has a low solubility in water, has a density different from water to provide separation therefrom, and forms a low boiling azeotrope with water, said azeotrope having an atmospheric boiling point below that of said glyoxylic acid ester to provide for separation of water from said ester.

18. A process as set forth in claim 17 wherein said azeotroping agent is selected from the group consisting of methylene dichloride, 1,1,1,-trichloroethane, and benzene.

19. A process as set forth in claim 18 wherein said azeotroping agent comprises methylene dichloride.

20. A process as set forth in claim 18 wherein oxygen is substantially excluded from said finishing column during said finishing azeotropic distillation operation.

21. A process as set forth in claim 20 wherein an inert gas purge is passed through said finishing column prior to said operation.

22. A process as set forth in claim 20 wherein a blanket of inert gas is maintained at the head of said finishing column during said operation.

23. A process as set forth in claim 16 wherein said azeotropic distillation operation is carried out at a substantially atmospheric head pressure.

24. A process as set forth in claim 23 wherein the temperature within said finishing column is measured at a control stage therein, said control stage being above the stage at which the glyoxylic ester fraction is withdrawn from the side of the column but below said uppermost stage, and said temperature is controlled by controlling addition of said azeotroping agent to said finishing column above said stage at which said glyoxylic acid ester fraction is withdrawn.

25. A process as set forth in claim 16 wherein said glyoxylic acid ester fraction is fed to said finishing column at between about the twentieth sieve tray and about the fortieth sieve tray.

26. A process as set forth in claim 16 wherein said substantially dehydrated glyoxylic acid fraction is withdrawn from said finishing column at between about the fifth sieve tray and about the fifteenth sieve tray.

27. A process as set forth in claim 26 wherein the temperature within said finishing column is measured at a control stage therein, said control stage being above the stage at which the substantially dehydrated glyoxylic ester fraction is withdrawn from the side of the finishing column but below said uppermost stage, and said temperature is controlled by controlling addition of said azeotroping agent to said finishing column above said stage at which said substantially dehydrated glyoxylic acid ester fraction is withdrawn.

28. A process as set forth in claim 27 wherein the temperature at the bottom of said column is controlled at between about 125° and about 150° C.

29. A process as set forth in claim 26 wherein said substantially dehydrated glyoxylic acid fraction constitutes about one fourth of the liquid flowing tohe stage at which said substantially dehydrated fraction is withdrawn.

30. A process as set forth in claim 29 wherein the temperature at the bottom of said finishing column is controlled at between about 125° and about 150° C.

* * * * *